United States Patent [19]

Chen et al.

[11] Patent Number: 5,684,889

[45] Date of Patent: Nov. 4, 1997

[54] PARAMETRIC IMAGE REPRESENTATION OF IMAGING AGENT KINETICS

[75] Inventors: Qin-Sheng Chen; George Sgouros, both of New York, N.Y.

[73] Assignee: Sloan-Kettering Institute for Cancer Research, New York, N.Y.

[21] Appl. No.: 431,291

[22] Filed: Apr. 28, 1995

[51] Int. Cl.$^6$ ................................................ G06K 9/00
[52] U.S. Cl. ................................ 382/128; 382/274
[58] Field of Search ........................ 382/133, 131, 382/132, 134, 128, 129, 130, 155, 162, 165, 168, 170, 181, 190, 209, 224, 254, 260, 270, 274, 275, 276, 286, 293, 302, 232, 236; 128/653.1, 654, 659; 364/413.26

[56] References Cited

U.S. PATENT DOCUMENTS

| | | | |
|---|---|---|---|
| 3,831,031 | 8/1974 | Barrett et al. | 250/363 |
| 4,181,939 | 1/1980 | Lyons | 128/654 |
| 4,891,844 | 1/1990 | Kiri | 382/132 |
| 4,947,850 | 8/1990 | Vanderkooi et al. | 128/654 |
| 5,027,817 | 7/1991 | John | 128/654 |
| 5,088,492 | 2/1992 | Takayama et al. | 128/654 |
| 5,261,406 | 11/1993 | Mackay et al. | 128/654 |

OTHER PUBLICATIONS

Berman, M, Weiss, M.F. and Shahn, E. (1962) Some formal approaches to the analysis of kinetic data in terms of linear compartmental systems, Biophys. J., 2:289–316.

Chen Q.S., Defrise, M. and Deconinck, F. (1994) Symmetric Phase–Only Matched Filtering of Fourier–Mellin Transforms for Image Registration and Recognition. IEEE Transactions on Pattern Analysis and Machine Intelligence, vol. 16, No. 12: 1156–1168.

Loevinger, R. and Berman, M. (1968) A schema for absorbed–dose calcualtions for biologically–distributed radionuclides, MIRD Phamphlet No. 1, J. Nucl. Med., (Supl No. 1): 7–14.

Loevinger, R., Budinger, T.F. and Watson, E.E. (1989) MIRD primer for absorbed dose calculations. New York: The Society of Nuclear Medicine (No Page Number).

Merickel, M. (1988) 3D reconstruction: the registration problem. Computer Vision, Graphics and Image Processing, 42:206–219; Academic Press Inc.

Phelps, M.E., Huang, S.C., Hoffman, E.J., Selin, M.S., Sokoloff, L. and Kuhl, D.E. (1979) Tomographic measurement of local cerebral glucose metabolic rate in humans with (F–18)2–Fluoro–2–Deoxy–D–Glucose Validation of method. Ann. Neurol., 6:371–388; Little, Brown & Company, Boston.

Raichle, M.E., Welch, M.J., Grubb, Jr., R.L., Higgins, C.S., Ter–Pogossian, M.M. and Larson, K.B. (1978). Measurement of regional substrate utilization rates by emission tomography, Science, 199:986–987.

Smith, E.M. (1970) General considerations in calculation of the absorbed dose of radiopharmaceuticals used in nuclear medicine, Medical Radionuclides: Radiation Dose and Effects, Cloutier, R.J., Edwards, C.L., Snyder, W.S., Eds., Oak Ridge, UDAEC Conf. 691212:17–28.

Thomas, S.R., Maxon, H.R. and Keriakes, J.G. (1976) In vivo quantitation of lesion radioactivity using external counting methods. Med. Phys., 3:253–255.

*Primary Examiner*—Leo Boudreau
*Assistant Examiner*—Bijan Tadayon
*Attorney, Agent, or Firm*—John P. White

[57] ABSTRACT

A method of imaging a characteristic of image intensity of an imaging agent in a subject consists of introducing the imaging agent into the subject and repetitively scanning the subject at each of a plurality of time intervals, so as to produce a plurality of time-sequenced images throughout the subject. Each of the time-sequenced images is then subdivided into a notional array of image elements such that there is a one-to-one correspondence between positions of image elements in the array and locations in the subject. Thereafter, a value of image intensity of the imaging agent at the corresponding location in the subject is determined for each image element in each of the time-sequenced images, the image elements in the arrays of successive time-sequenced images being in register with each other with respect to the locations. The determined image intensity values of image elements of plural time-sequenced images, in register with each other, are then combined to generate an image of the characteristic of image intensity of the imaging agent.

20 Claims, 5 Drawing Sheets
5 of 5 Drawing(s) in Color

PARAMETRIC IMAGE REPRESENTATION OF IMAGING AGENT KINETICS

The invention disclosed herein was made with Government support under NCI Core Grant No. 08748 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

This invention relates to imaging methods, and more particularly to methods of imaging characteristics of image intensity of an imaging agent in a subject.

In the conventional approach to extracting kinetic information from a set of longitudinal scintigraphic images, a series of contours are drawn around previously identified areas of interest. The total counts in each area are plotted against time and each such time-activity curve is fit to an exponential expression whose parameters generally include the clearance or uptake rate of the administered imaging agent in the chosen area. The information in such a set of images is thereby reduced to a single set of values representing the clearance or uptake rates of an imaging agent such as a radionuclide averaged over a particular area (Berman et al., 1962; Loevinger and Berman, 1968; and Smith, 1970). Aside from radionuclide dosimetry, such kinetic information has not been routinely considered in terms of patient diagnosis and management and the potential clinical value of such information has not been assessed. To a large extent, this may be ascribed to the difficulty of presenting such kinetic information in a comprehensive and easily interpretable manner.

This invention discloses a technique for generating images that provide kinetic information over the whole-body. Using this methodology, a series of longitudinal scintigraphic studies are converted to a single image in which each pixel value represents the clearance or uptake rate of the imaging agent. Corresponding images of the initial activity in each pixel predicted by the fits (i.e., the intercepts) and the residence time/cumulated activity in each pixel are also generated.

The methodology has been applied to a series of longitudinal images obtained from patients with thyroid cancer. Using this approach it is possible to identify regions of rapid clearance or uptake against the background of whole-body clearance. Since kinetic information is provided over the whole image, regions of unexpected uptake or clearance that would not otherwise be highlighted are easily identified in such images.

SUMMARY OF THE INVENTION

This invention embraces techniques for generating images that provide kinetic information over the whole-body. Using this methodology, a series of longitudinal scintigraphic studies are converted to a single image subdivided into an array of image elements (e.g. pixels) in which each pixel value represents the clearance or uptake rate of the imaging agent. Corresponding images of the initial activity in each pixel predicted by the fits (i.e., the intercepts) and the residence time/cumulated activity in each pixel are also generated.

The methodology has been applied to a series of longitudinal images obtained from patients with thyroid cancer. Using this approach it is possible to identify regions of rapid clearance or uptake against the background of whole-body clearance. Since kinetic information is provided over the whole image, regions of unexpected uptake or clearance that would not otherwise be highlighted are easily identified in such images.

The present invention provides a method of imaging a characteristic of image intensity of an imaging agent in a subject, comprising:

(a) introducing the imaging agent into the subject;

(b) thereafter repetitively scanning the subject at each of a plurality of time intervals, so as to produce a plurality of time-sequenced images of image intensity of the imaging agent throughout the subject;

(c) subdividing each of the time-sequenced images into a notional array of image elements such that there is a one-to-one correspondence between positions of image elements in the array and locations in the subject and determining, for each image element in each of the time-sequenced images, a value of image intensity of the imaging agent at the corresponding location in the subject, the image elements in the arrays of successive time-sequenced images being in register with each other with respect to said locations; and (d) combining the so determined image intensity values of image elements of plural time-sequenced images, in register with each other, so as to generate an image of said characteristic.

The present invention provides methods useful for detection and diagnosis of abnormal or diseased states such as cancer. It also provides methods for developing a treatment plan for the subject. Lastly, the present invention provides methods for assessing or predicting the responsiveness of the abnormal or diseased state to an appropriate treatment.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

The present invention provides a method of imaging a characteristic of image intensity of an imaging agent in a subject, comprising:

(a) introducing the imaging agent into the subject;

(b) thereafter repetitively scanning the subject at each of a plurality of time intervals, so as to produce a plurality of time-sequenced images of image intensity of the imaging agent throughout the subject;

(c) subdividing each of the time-sequenced images into a notional array of image elements such that there is a one-to-one correspondence between positions of image elements in the array and locations in the subject and determining, for each image element in each of the time-sequenced images, a value of image intensity of the imaging agent at the corresponding location in the subject, the image elements in the arrays of successive time-sequenced images being in register with each other with respect to said locations; and (d) combining the so determined image intensity values of image elements of plural time-sequenced images, in register with each other, so as to generate an image of said characteristic.

The term "characteristic of image intensity" is used herein to designate attributes of image intensity determinable from a succession of images or measurements of image intensity obtained over time, and includes without limitation, the rate-of-change of image intensity, the initial take-up image intensity, and the cumulative image intensity.

The term "subject" includes, but is not limited to, animals and human beings, and may mean either the whole body (e.g. of an animal or human being) or a region of interest therein.

The term "notional array of image elements" includes, but is not limited to, an array (e.g. rectangular matrix) of pixels or like discrete elements that comprise an image.

The term "combining" is used herein to designate operations whereby a characteristic of image intensity is determined from a succession of images or measurements of image intensity obtained over time.

Image intensity, for a given introduction of imaging agent, is a function of concentration of imaging agent; i.e., greater or lesser image intensity values, in different areas within the subject being imaged, respectively correspond to greater or lesser concentrations of imaging agent at these different areas.

"Plurality of time-sequenced images" means a succession of images respectively obtained by scanning the subject at different times, separated from each other by time intervals.

In one embodiment of the present invention, the characteristic of image intensity is the rate-of-change of image intensity of the imaging agent. The term "rate-of-change of image intensity" is used herein to mean the changes in the intensity of the imaging agent over time.

In another embodiment of the invention, the characteristic of image intensity is the initial take-up image intensity value. The term "initial take-up image intensity" is used herein to mean the image of the intensity of the initial uptake of the imaging agent.

In yet another embodiment of the invention, the characteristic of image intensity is the cumulative image intensity. The term "cumulative image intensity" is used herein to mean the image of the cumulated intensity of the imaging agent over time. Throughout the application the terms "cumulative image intensity", "cumulated activity image", and "residence time image" are used interchangeably.

In one embodiment of the invention, the imaging agent is introduced orally, intravenously, intraperitoneally, intralymphatically, or subcutaneously. The oral, intravenous, intraperitoneal, intralymphatic, or subcutaneous introduction of the imaging agent into the subject is known to those skilled in the art.

The time-sequenced images can be generated at a time-interval that is appropriate with respect to the overall rate-of-change in intensity of the imaging agent. One non-limiting example of such a time sequence, having utility in particular cases, is 12, 24, 48 and 72 hours after introduction of the imaging agent to the subject. The generated images are registered using a variety of techniques including a symmetric phase-only matched filter technique.

In another embodiment of this invention, the characteristic of image intensity of the imaging agent in the subject is generated, displayed and represented along with a color-coded scale.

In one embodiment of the present invention, the imaging agent is a radioisotope. $^{131}$I is an example of a radioisotope that can be used wherein its amount is from 0.1 mCi to about 300.0 mCi.

In another embodiment of the invention, the image of the characteristic of image intensity of the imaging agent in the subject is generated by mathematically fitting decay corrected intensity values of image intensity of the imaging agent at the corresponding location of each of the time-sequenced images in the subject.

The present invention further provides for a method wherein the image of the characteristic of image intensity of the imaging agent in the subject is used to assess the subject's administered imaging agent kinetics.

The present invention still further provides a method wherein the image of the characteristic of image intensity of the imaging agent in the subject is used to monitor the kinetics and the delivery of an appropriate drug when tagged with the imaging agent.

In one embodiment, the present invention provides a method to obtain information regarding behavior of the imaging agent in normal tissues.

In one another embodiment, the present invention provides a method to detect or diagnose abnormal or diseased states.

In a related embodiment, it also provides a method to detect cancer.

In another embodiment, the present invention further provides a method to develop a treatment plan for the subject.

Lastly, the present invention provides a method to assess or predict the responsiveness of the abnormal or diseased state to an appropriate treatment.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Image Acquisition and Conjugate View Generation: Using a dual-head scanner (one example being the Adac Dual-Head Genesys scanner commercially available from Adac, Inc., Milpitas, Calif.) three of four sets of anterior and posterior planar gamma camera images, separated by approximately 24 hours, were obtained in a series of patients with thyroid cancer following oral administration of approximately 10 mCi $^{131}$I. Each of the posterior images was digitally inverted to create a pseudo-anterior image. The anterior image and its pseudo-anterior counterpart, were registered (brought into register with each other) using a symmetric phase-only matched filter (Chen et al., 1994) to compensate for possible misalignment of images during acquisition or manipulation prior to storage. A conjugated view image of the anterior, and registered pseudo-anterior pair was then obtained (Thomas et al., 1976). The calibration standard that was placed in the field of view was removed digitally prior to image registration.

The Symmetric Phase-Only Matched Filter and Image Registration: The symmetric phase-only matched filter (SPOMF) technique was used for image registration of the planar images. Details regarding this technique have been described previously (Chen et al., 1994). The technique is summarized, briefly as follows. For two planar images, $I_1(x,y)$ and $I_2(x,y)$, assume one is a translated replica of the other with offset $(x_0, y_0)$:

$$I_2(x,y) = I_1(x-x_0, y-y_0) + n(x,y) \tag{1}$$

where n(x,y) denotes a sample of zero mean, stationary random noise field. If the Fourier transforms of these two images are defined by $S_1(u,v) = F\{I_1(x,y)\}$ and $S_2(u,v) = F\{I_2(x,y)\}$ with $F\{.\}$ denoting the Fourier transformation, the symmetric phase-only matched filter (SPOMF) to match $I_2$ to $I_1$ has the form:

$$Q(u,v) = \frac{S_1(u,v)}{|S_1(u,v)|} \cdot \frac{S^*_2(u,v)}{|S_2(u,v)|} \tag{2}$$

Where $S^*(u,v)$ is the complex conjugate of $S(u,v)$. The maximum of the inverse Fourier transform corresponds to the relative image translation.

Due to differences in uptake and clearance of the radionuclide in different tissues, the radioactivity distribution over the whole body changes inhomogeneously over time and so do the corresponding images. Therefore, detecting patient movement in longitudinal images using a global technique is not reliable. Instead, a set of sub-regions that exhibited a consistent pattern of radioactive distribution over time were selected from the longitudinal images. The local displacement of each sub-region over time was estimated using the SPOMF technique, described above (Chen et al., 1994). Once the displacement had been estimated for each sub-region, the global image translation, rotation, and scaling were estimated by performing a 2-D linear least squares fit (Merickel, 1988). Each planar image was then realigned according to the estimated parameters.

Parametric Image Generation: After registration, the value in each pixel, over time, corresponds to the same anatomical region. It is then possible to obtain the kinetic parameters for each pixel by fitting its value, A(x,y), to an exponential function, $A_t(x,y)$, at the same point over time t:

$$A_t(x,y) = A_0(x,y) \cdot e^{-\lambda(x,y) \cdot t} \tag{3}$$

By performing this fit for each pixel, two parametric images of radiopharmacokinetics, representing the intercept, $A_0(x,y)$, and the clearance rate, $\lambda(x,y)$, are derived. Prior to fitting, the images sets are decay-corrected so that the $\lambda(x,y)$ images represent biological instead of effective clearance rates. A cumulated activity or residence time image may then be obtained by including the decay rate, $\lambda_p$, of the radionuclide in the exponential and analytically integrating the equation for each pixel:

$$\tilde{A}(x,y) = \int A_0(x,y) \cdot e^{-(\lambda(x,y) + \lambda_p) \cdot t} dt, \tag{4}$$

The corresponding residence time image is obtained from the cumulated activity image by performing a pixel-by-pixel division of $\tilde{A}(x,y)$ by $A_0(x,y)$.

Figure 1A:
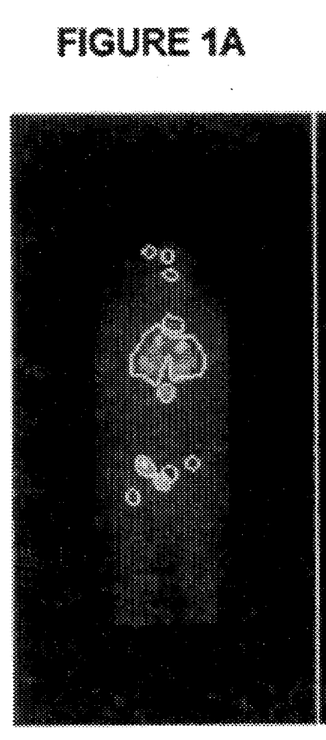
FIGS. 1A, 1B, and 1C are a set of conjugate view images of a thyroid cancer patient. The images were acquired at 24 (A), 48 (B) and 72 (C) hours after administration of 10 mCi $^{131}$I. Superimposed upon these images are a set of contours initially drawn on the 24 hour image (A).
Figure 1B:
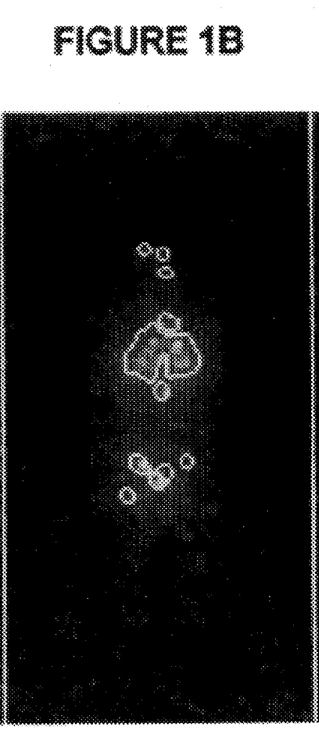
Figure 1C:
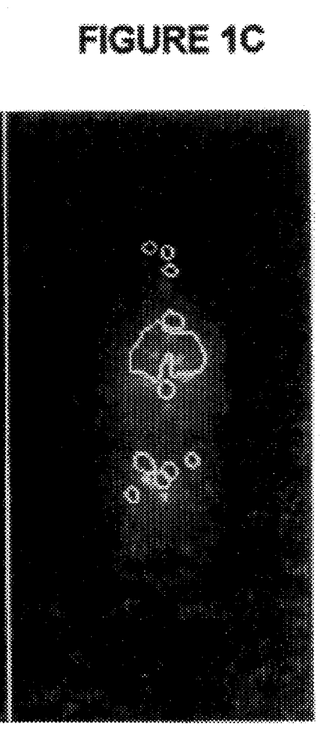

Registration: FIGS. 1A, 1B, 1C, 2A, 2B and 2C depict a series of conjugate-view images obtained at 24, 48 and 72 hours after administration of 10 mCi $^{131}$I in a patient with metastatic thyroid carcinoma. Using the 24 hour image (FIG. 1A), a set of contours were drawn around several regions of interest. This contour set is superimposed upon the unregistered 48 and 72 hour images (FIGS. 1B, 1C). As expected, significant mismatches are observed between contours drawn using the 24 hour image and the regions of interest in the 48 and especially the 72 hour images.

Figure 2A:
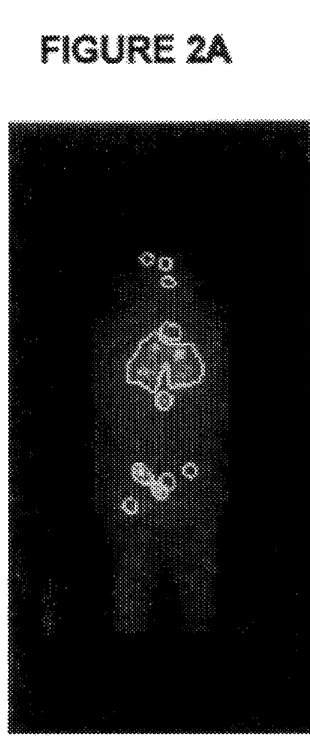
FIGS. 2A, 2B, and 2C are, respectively, the conjugate view images of the thyroid cancer patient in FIG. 1A, FIG. 1B, and FIG. 1C after registration. The images were acquired at 24 (A), 48 (B) and 72 (C) hours after administration of 10 mCi $^{131}$I.
Figure 2B:
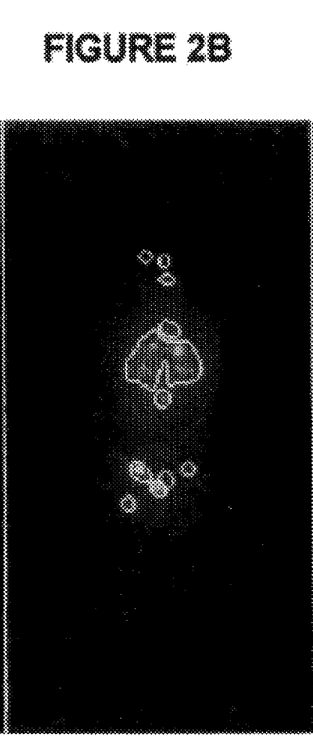
Figure 2C:
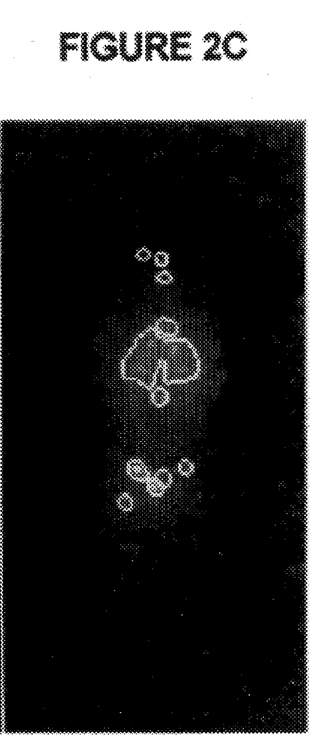

By following the procedure outlined in the methods, the relative shifts of smaller sub-images were calculated. The centers of these 3 sub-images and their relative displacement in the 48 and 72 hour images are listed in Table 1. This information was then used to estimate global translations, rotations, and scale changes for the second and third images. This information is listed in Table 2. FIGS. 2A, 2B, and 2C depict the contours drawn in FIGS. 1A, 1B, and 1C but for images that have been registered to the 24 hour image. As may be seen, the contours at each time point are now consistent with the regions of interest identified at 24 hours.

Figure 3A:
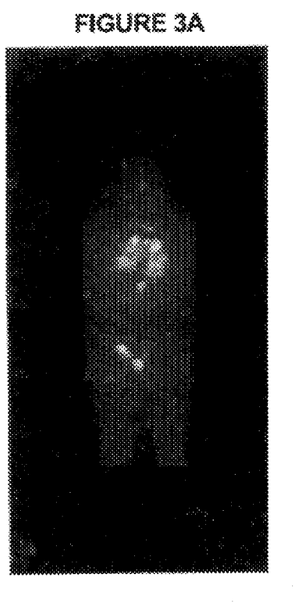
FIGS. 3A, 3B, and 3C are, respectively, the intercept image (A) obtained by fitting the images in FIG. 2A, FIG. 2B, and FIG. 2C to a single exponential function; the corresponding rate image (B) for which the scale is chosen so that blue areas, going from black to bright represent regions of increasing clearance rate, and red areas, also going from black to bright represent regions of increasing uptake rate; and the cumulated activity image (C), derived from (A) and (B).
Figure 3B:
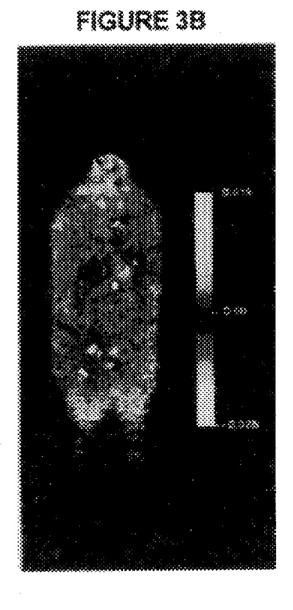
Figure 3C:
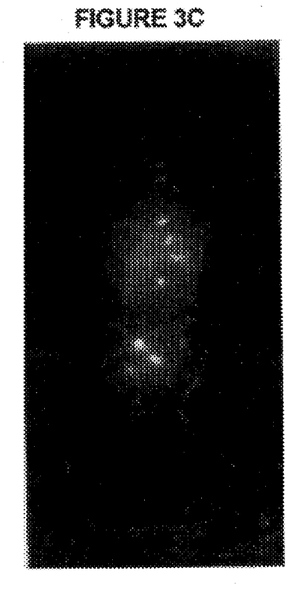

Parametric Images: The "intercept", "rate" and "cumulated activity" images obtained using the images depicted in FIGS. 2A, 2B, and 2C are shown in FIGS. 3A, 3B, and 3C, respectively. It is important to note that the intercept image (FIG. 3A) provides a measure of the initial activity in each region based upon the fitted equation. Since a limited number of imaging time points were available, it was not possible to characterize the rising component of the time-activity curve. By comparing FIG. 3A with FIG. 3C, it is easy to distinguish between regions exhibiting a high initial Tables:

TABLE 1

The centers of the sub-images on different days. Matrix size of image is 256 × 256, the origin is at the upper left hand corner.

| | Time Post-Administration | | |
|---|---|---|---|
| | 24 hrs | 48 hrs | 72 hrs |
| Sub-image 1 | (132, 67) | (130, 67) | (131, 74) |
| Sub-image 2 | (128, 153) | (129, 154) | (129, 161) |
| Sub-image 3 | (134, 88) | (132, 89) | (132, 94) |

TABLE 2

The translation, rotation, and scaling values used to register the images.

| | Translation (pixels) | Rotation | Scale change |
|---|---|---|---|
| 48 hrs image | (0.955, 1.062) | −2.146° | 0.998 |
| 72 hrs image | (−0.045, 7.062) | −2.146° | 0.998 | uptake but low total retention and regions that exhibit a high overall retention. A region of high initial uptake at the center of the pelvis, that is adjacent to two brighter regions in FIG. 3A, may be easily distinguished from disease and most likely corresponds to bladder, since this region is absent from the cumulated activity image in FIG. 3C. Similar observations may be made by comparing the radioactivity distribution in the head between FIG. 3A and FIG. 3C. Several regions of increased intensity in the head that appear in FIG. 3A are not observed in FIG. 3C. A comparison of these two images also highlights the increase in liver uptake over time and the resulting overall retention in the liver which appears faintly below the patient's right lung region in FIG. 3C but not in FIG. 3A. The image depicted in FIG. 3B provides information regarding the clearance rates in different regions. Since several regions exhibited no clearance and, in some cases, uptake of radioactivity was observed over the time course of image collection, a red-blue intensity scale is used in which blue represents clearance and red represents uptake. No change in radioactivity over time is represented by black. First, it is clear from the image that there is considerable variability in radionuclide kinetics between different regions. The previously identified region of the bladder is depicted in bright blue, indicating a relatively rapid clearance rate. This region is adjacent to several "hot" red regions which clearly identify sites of disease. Except for the three small sites of radionuclide uptake that are also observed in the cumulated activity image, the clearance rate in the head, overall, is more rapid than that in the chest or abdomen (brighter blue vs. darker blue). The combination of images depicted in FIGS. 3A, 3B, and 3C may be used to understand the uptake properties of individual tumors. If one compares, for example the two brightest lesions in the upper portions of the lungs with the lesions in the pelvis several important observations emerge. In FIG. 3A, the intensity of the lung lesions indicates a radioactivity concentration that is greater than that observed in the pelvic lesions. The rate image in FIG. 3B, however, indicates that the radioactivity concentration in the lung lesions is decreasing at approximately the whole-body clearance rate whereas the concentration in the pelvic lesions is increasing. The balance between initial uptake and clearance rate is represented in FIG. 3C, where the intensity of the lung lesions is considerably less than that in the pelvic lesions. Based upon this brief analysis of the information provided by FIGS. 3A, 3B, and 3C, one may predict a greater therapeutic effect in the pelvic lesions than in the upper lung lesions. It is important to note that although the image in FIG. 3C provides information that is related to the absorbed dose, such images may not be interpreted as absorbed dose images, directly, since information regarding the mass of each lesion is not provided.

Figure 4A:
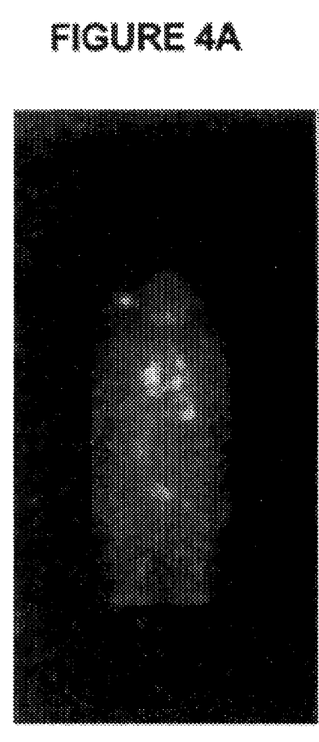
FIGS. 4A, 4B, and 4C are images of a set of registered, conjugate view images of another thyroid cancer patient acquired at 24 (A), 48 (B), and 72 (C) hours.
Figure 4B:
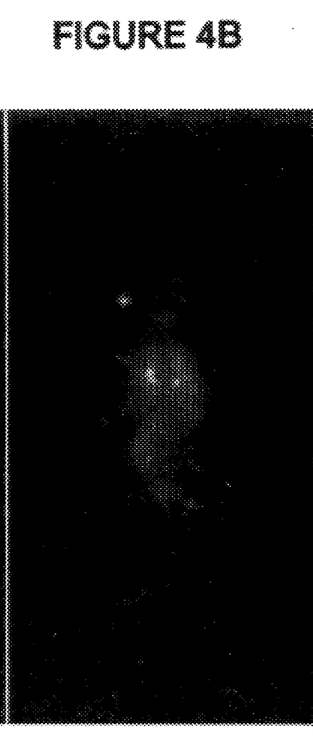
Figure 4C:
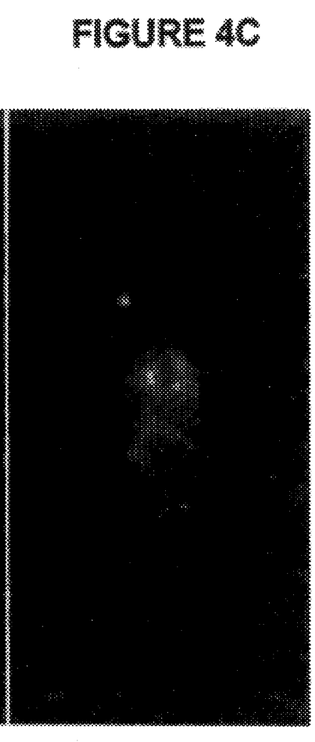
Figure 5A:
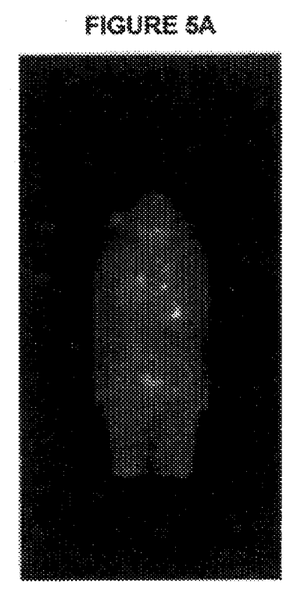
FIGS. 5A, 5B, and 5C are, respectively, images of the intercept (A), rate (B), and cumulated activity (C) obtained from the images shown in FIGS. 4A, 4B, and 4C.
Figure 5B:
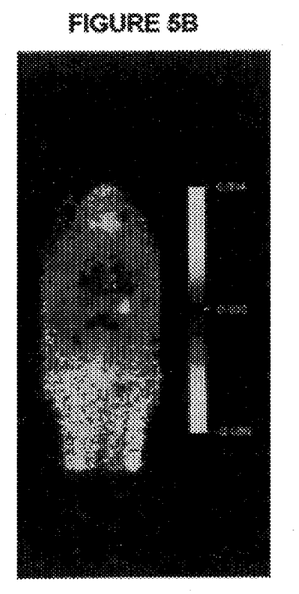
Figure 5C:
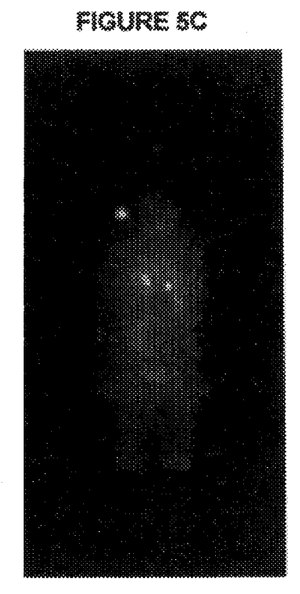

FIGS. 4A, 4B, 4C, 5A, 5B, and 5C depict the corresponding set of images for another thyroid cancer patient. Registered, conjugate-view images at 24, 48 and 72 hours post-injection are shown in FIGS. 4A, 4B, and 4C. FIGS. 5A, 5B, and 5C depict the intercept, rate and cumulated activity images, respectively. As before, the images in FIGS. 5A, 5B, and 5C may be used to help understand the differential kinetics of $^{131}$I in this patient. It is possible, for example, to distinguish within the diffuse disease in the lungs a small region that exhibits an increase in radioactivity concentration during the measured time-interval. This is seen in FIG. 5B as a small region of bright red within the darker blue background of diminished clearance in the lung metastases. The balance between initial uptake and the rate of clearance may again be highlighted for two different regions. In FIG. 5A, one may easily identify a region of high radioactivity concentration below the patient's left lung that corresponds to the stomach. In FIG. 5B, this region is clearing with a rate that is similar to that of the body, overall. In FIG. 5C, this region is visible but with an intensity that is considerably lower than that of the diffuse disease in the lungs. This indicates that although the initial uptake is comparable to that observed in the lung metastases, the total cumulated activity in the stomach is lower, once the clearance rate is taken into account. In a similar manner, the consequences of a clearance rate that appears to be similar to that in the metastases may be assessed. A dark, semi-elliptical, band below the lungs is observed in FIG. 5B, suggesting that radionuclide in this region clears as slowly as in the metastases. Since this region, which may be identified as the transverse colon is not observed in FIG. 5A, the initial radioactivity concentration is comparatively low. Correspondingly, the cumulated activity result shown in FIG. 5C indicates that although the clearance rate is slow, the cumulated activity is low relative to that of the lung metastases.

In most cases, changes in the radioactivity distribution of a particular agent, obtained from multiple nuclear medicine studies following a single administration, are assessed by placing the individual images adjacent to each other and simply examining each, one at a time, and as a whole. Such an analysis provides a qualitative understanding of the relative changes in radioactivity distribution over time. Quantitative assessments are obtained by drawing contours over individual regions for each image and from such time-activity data extracting clearance rates or half-times and intercepts. The methodology described herein provides an additional approach which essentially combines the two. Quantitative information—the clearance rates, intercepts and cumulated activities—are provided, but as parametric images from which clinical information may be more easily extracted.

An important distinction must be made between other examples of parametric images, such as, parametric images of glucose metabolic rate, obtained using $^{18}$F-fluoro-deoxyglucose with positron emission tomography, and the current methodology. In other approaches, the parametric image is generally obtained by translating a single image set, obtained at a single point in time, into a rate image using mathematical modeling (Raichle et al., 1978; and Phelps et al., 1979). The parametric images that have been generated for the $^{131}$I thyroid cancer patients, were obtained by directly measuring and fitting the radioactivity distribution over time.

Several important elements must be considered in assessing the potential value and accuracy of this methodology. The accuracy of the estimated parameters depends upon: the number of planar images available at different time points for fitting, the fidelity of the image registration procedure, the number of counts in each pixel and the equation that is used to define the fitted parameters. All of these items are related since as the number of images obtained over time increases, better resolution of the kinetics is achieved thereby potentially requiring a more detailed equation for fitting. With an increase in image number, greater demands are placed on the registration procedure since more images must be registered. As later time points are added to a longitudinal imaging study, the error associated with the diminished number of counts in each pixel increases.

The most fundamental concern relates to the equation that is used for fitting. If an equation with too many parameters is required to adequately fit the data, or if the kinetics in different anatomical regions are described by different functions, then the methodology becomes more difficult to implement and, more importantly, inappropriate. In practice, this is very rarely the case. In essentially all cases, the macroscopic clearance kinetics of radiolabeled agents may be described by an exponential equation (Loevinger et al., 1989). If imaging is performed early relative to the uptake of the labeled agent, an uptake term may also be necessary. Given a sufficient number of images, neither situation presents a difficulty in the implementation of this method. In assessing the technique's utility it is important to distinguish between the ability to apply a kinetic model to data measured over a particular region and the ability to express changes in radioactivity in the region using an exponential equation. The two are not mutually exclusive.

The image registration technique that was implemented in these studies is particularly appropriate for registration of nuclear medicine images that are collected over time following a single injection. Such images have the properties of low spatial resolution and low signal to noise ratio. Matching of such images based upon image intensity may not be reliable. The technique that was employed herein uses the Fourier spectral phase which preserves shape rather than intensity information. Although the signal intensity is expected to change over time, if the underlying shape of the radioactivity distribution is preserved, the spectral phase approach can better utilize such information.

A methodology that yields kinetic information over a whole image in parametric form was developed and implemented. The resulting images provide a visual and comprehensive assessment of radionuclide kinetics throughout the whole body. When presented in this way, kinetic information is more easily interpreted and may have a greater impact on patient care.

REFERENCES

1. Berman M, Weiss M F, Shahn E. (1962) Some formal approaches to the analysis of kinetic data in terms of linear compartmental systems. *Biophys. J.*, 2:289–316.
2. Loevinger R, Berman M. (1968) A schema for absorbed dose calculations for biologically-distributed radionuclides. MIRD Pamphlet No 1, *J. Nucl. Med.*, (Suppl No. 1): 7–14.
3. Smith E. M. (1970) General considerations in calculation of the absorbed dose of radiopharmaceuticals used in nuclear medicine. In *Medical Radionuclides:* Radiation Dose and Effects, Cloutier R. J., Edwards C. L., Snyder W. S., eds, Oak Ridge, USAEC Conf 691212: 17–28.
4. Chen Q. S., Defrise M., Deconinck F. (1994) Symmetric Phase-Only Matched Filtering of Fourier Mellin Transforms for Image Registration and Recognition. *IEEE Transactions on Pattern Analysis and Machine Intelligence*, Vol. 16, No. 12: 1156–1168.
5. Thomas S. R., Maxon H. R., Keriakes J. G. (1976) In vivo quantitation of lesion radioactivity using external counting methods. *Med. Phys.*, 3:253–255.
6. Merickel M. (1988) 3D reconstruction: The registration problem. *Computer Vision Graphics and Image Processing*, 42:206–219.
7. Raichle M. E., Welch M. J., Grubb Jr R. L., Higgins C. S., Ter-Pogossian M. M., Larson K. B. (1978) Measurement of regional substrate utilization rates by emission tomography. *Science*, 199:986–987.
8. Phelps M. E., Huang S. C., Hoffman E. J., Selin M. S., Sokoloff L., Kuhl D. E. (1979) Tomographic measurement of local cerebral glucose metabolic rate in humans with (F-18)2-Fluoro-2-Deoxy-d-Glucose: Validation of method. *Ann. Neurol.*, 6:371–388.
9. Loevinger R., Budinger T. F., Watson E. E. (1989) MIRD primer for absorbed dose calculations. New York: The Society of Nuclear Medicine.

What is claimed is:

1. A method of imaging a characteristic of image intensity of an imaging agent in a subject, comprising:

(a) introducinq the imaging agent into the subject;

(b) thereafter repetitively scanning the subject at each of a plurality of time intervals, so as to produce a plurality of time-sequenced images of image intensity of the imaging agent throughout the subject;

(c) subdividing each of the time-sequenced images into a notional array of image elements such that there is a one-to-one correspondence between positions of image elements in the array and locations in the subject and determining, for each image element in each of the time-sequenced images, a value of image intensity of the imaging agent at the corresponding location in the subject, the image elements in the arrays of successive time-sequenced images being in register with each other with respect to said locations; and (d) combining decay corrected intensity values of the so determined image intensity values of image elements of plural time-sequenced images, in register with each other, so as to generate an image of said characteristic.

2. The method according to claim 1, wherein said characteristic is rate-of-change of image intensity of said imaging agent.

3. The method according to claim 1, wherein said characteristic is initial take-up image intensity value.

4. The method according to claim 1, wherein said characteristic is cumulative image intensity.

5. The method of claim 1, wherein said imaging agent is introduced orally, intravenously, intraperitoneally, intralymphatically, or subcutaneously.

6. The method of claim 1, wherein said time-sequenced images are generated at a time-interval that is appropriate with respect to the overall characteristics of the imaging agent.

7. The method of claim 1, wherein the generated images are registered using a symmetric phase-only matched filter technique.

8. The method of claim 1, further comprising displaying of said characteristic of image intensity of said imaging agent in the subject.

9. The method of claim 8, wherein said displayed image of said characteristic of image intensity of said imaging agent in the subject is represented along with a color-coded scale.

10. The method of claim 1, wherein said imaging agent is a radioisotope.

11. The method of claim 10, wherein said radioisotope is $^{131}$I.

12. The method of claim 11, wherein the amount of $^{131}$I is from 0.1 mCi to about 300.0 mCi.

13. The method of claim 12, wherein the amount of $^{131}$I is from about 5 mCi to 15 mCi.

14. The method of claim 1, wherein the image of said characteristic of image intensity of said imaging agent in the subject is used to detect or diagnose abnormal or diseased state.

15. The method of claim 1, wherein the image of said characteristic of image intensity of said imaging agent in the subject is used to assess the subject's administered imaging agent kinetics.

16. The method of claim 1, wherein the image of said characteristic of image intensity of said imaging agent in the subject is used to monitor the kinetics and the delivery of an appropriate drug when tagged with said imaging agent.

17. The method of claim 1, wherein the image of said characteristic of image intensity of said imaging agent in the subject is used to obtain information regarding behavior of the imaging agent in normal tissues.

18. The method of claim 1, wherein the image of said characteristic of image intensity of said imaging agent in the subject is used to assess or predict the responsiveness of said abnormal or diseased state to an appropriate treatment.

19. The method of claim 1, wherein said diseased state is cancer.

20. The method of claim 1, wherein the image of said characteristic of image intensity of said imaging agent in the subject is used to develop a treatment plan for the subject.

* * * * *